(12) United States Patent
Cohen et al.

(10) Patent No.: US 8,229,764 B2
(45) Date of Patent: Jul. 24, 2012

(54) METHOD OF IDENTIFYING DATA RELATING TO INDIVIDUALS IN ORDER TO CHAIN SAID DATA

(75) Inventors: Olivier Cohen, Grenoble (FR); Catherine Quantin, Saint Apollinare (FR)

(73) Assignee: Universite de Bourgogne, Dijon Cedex (FR)

( * ) Notice: Subject to any disclaimer, the term of this patent is extended or adjusted under 35 U.S.C. 154(b) by 918 days.

(21) Appl. No.: 11/683,003

(22) Filed: Mar. 7, 2007

(65) Prior Publication Data

US 2007/0204066 A1 Aug. 30, 2007

Related U.S. Application Data

(63) Continuation of application No. PCT/FR2005/002252, filed on Sep. 9, 2005.

(30) Foreign Application Priority Data

Sep. 9, 2004 (FR) .................................. 04 09584

(51) Int. Cl.
*G06F 19/00* (2006.01)
*G06Q 50/00* (2006.01)

(52) U.S. Cl. .......................................................... 705/3

(58) Field of Classification Search .................. 705/2, 4, 705/51; 707/104.1; 709/203; 370/336; 235/379; 713/176; 380/24

See application file for complete search history.

(56) References Cited

U.S. PATENT DOCUMENTS

| | | | |
|---|---|---|---|
| 4,852,165 A * | 7/1989 | Copella et al. ................... | 705/72 |
| 5,956,329 A * | 9/1999 | Pernice et al. .................. | 370/336 |
| 6,449,621 B1 * | 9/2002 | Pettovello ............................. | 1/1 |
| 2002/0010679 A1 * | 1/2002 | Felsher ............................ | 705/51 |
| 2002/0033415 A1 * | 3/2002 | Cummins ..................... | 235/379 |
| 2002/0042879 A1 * | 4/2002 | Gould et al. ................... | 713/176 |
| 2004/0044730 A1 * | 3/2004 | Gockel et al. ................. | 709/203 |

FOREIGN PATENT DOCUMENTS

| | | | |
|---|---|---|---|
| WO | WO 94/12943 | * | 6/1994 |
| WO | WO 01/09701 | | 2/2001 |
| WO | WO 02/05061 | | 1/2002 |
| WO | WO 03/034274 A1 | * | 4/2003 |

OTHER PUBLICATIONS

International Search Report from International Application No. PCT/FR2005/002252, Filed Sep. 9, 2005, with a mailing date of Mar. 23, 2006.

* cited by examiner

*Primary Examiner* — Gerald J. O'Connor
*Assistant Examiner* — John Pauls
(74) *Attorney, Agent, or Firm* — Alston & Bird LLP

(57) ABSTRACT

A method of identifying data relating to individuals in order to establish chains in said data, the method consisting, in a local center for collecting data, in creating an encoded first identifier of an individual from identification data of said individual, and of said individual's father and mother, in transmitting said first identifier to a central unit, and in said central unit creating an encoded second identifier which is recorded in a database, and in establishing chains in the data by comparing the second identifiers recorded in the database. The invention applies to treating data concerning individuals and having a family component.

15 Claims, 3 Drawing Sheets

METHOD OF IDENTIFYING DATA RELATING TO INDIVIDUALS IN ORDER TO CHAIN SAID DATA

CROSS-REFERENCE TO RELATED APPLICATIONS

This application is a continuation of International Application No. PCT/FR2005/002252, filed Sep. 9, 2005, which claims priority from French Patent Application No. 0409584, filed Sep. 9, 2004, which are hereby incorporated herein by reference.

The invention relates to a method of identifying data relating to individuals in order to chain the data by means of a data processor system comprising local centers for collecting data, a central unit for aggregating data, and data transmission means between the local centers and the central unit.

BACKGROUND OF THE INVENTION

The data relating to individuals, in which data chains are to be made, may particularly but not exclusively comprise medical information.

At present, medical centers are equipped with computer systems having databases recording data contained in patient dossiers and used with more or less complex software for performing searches, sorts, aggregations, classifications, statistics, etc.

This processing is generally sufficient for managing patient dossiers in medical centers and hospitals, but it does not satisfy the needs of certain specialized centers such as genetic centers where the data to be recorded about an individual needs to include a component enabling a family dimension to be reconstituted, as is essential for studying genetic diseases, complex multi-factor diseases, and pharmacogenetics.

Reconstituting such family dimensions requires data relating to individuals of a given family to be chained in a manner that is reliable and certain. It is also necessary to be able to perform chaining of data relating to a given individual when the data is recorded in different centers.

It is also necessary to be able to encode or encrypt said data so as to ensure confidentiality, while also complying with regulations in force giving patients access to medical data that concerns them.

OBJECTS AND SUMMARY OF THE INVENTION

A particular object of the invention is to satisfy that need.

To this end, the invention provides a method of identifying data relating to individuals in order to establish chains of said data by means of servers, databases, and data transmission means, the method consisting in:

using a data processor system comprising local centers for collecting data, each having a server and a local database, a central unit for aggregating data and equipped with a server and a central database, and data transmission means between the local centers and the central unit, each local center having means for creating an encoded first identifier of an individual by applying an encoding algorithm to identification data of the individual, such as the individual's surname, first name, and date of birth, and to identification data of the individual's father and mother, such as their surnames, first names, and dates of birth;

in using the above-mentioned transmission means to transmit said encoded first identifier with an order number and an identifier of the local center to the central unit which includes means for creating an encoded second identifier of the individual by applying an encoding algorithm to the encoded first identifier, and to record the encoded second identifier in the central database in the place of the encoded first identifier, together with the correspondence between the second identifier, the above-mentioned order number of the first identifier, and the identifier of the local center; and in comparing the second identifiers in the central unit in order to establish individual and family chains of the data.

In the method of the invention, creating an identifier for an individual from identification data of that individual together with identification data of that individual's father and mother, makes it possible to undertake family chaining of data concerning the individual, and concerning the father and the mother merely by comparing the identifiers, and also enables individual chaining to be undertaken on data relating to one individual, and enables this to be done in a manner that is certain and reliable, avoiding erroneous chains.

It can be considered that the risk of confusion between different individuals is zero when the identifiers of those individuals comprise three triplets of variables, i.e. a triplet of identification data for the individual, a triplet of identification data for the father, and a triplet of identification data for the mother.

It has already been demonstrated in numerous studies that the most reliable identification data are surname, given name, and date of birth (where surname means the surname at birth and not a customary name or a married name, and where given name means the first given name of an individual and not a second or third given name or a nickname).

When in accordance with the invention, an identifier of an individual is created from the individual's surname, first name, and date of birth, together with the surnames, first names, and dates of birth of that individual's father and mother, the possibility of two different individuals having the same identifier can be considered as zero (in the absence of data-inputting errors).

Furthermore, creating an encoded first identifier in the local center for collecting data ensures that the data recorded in the database of the local center is anonymous, and creating an encoded second identifier in the central unit from the encoded first identifier, serves to protect the data recorded in the database of the central unit and provides it with strict anonymity, even against people having knowledge of the encoding algorithm used for creating the first identifier, and also against people having knowledge of the encoding algorithm used for creating the second identifier, since that algorithm is applied to encoding data that is already encoded and anonymous.

According to another characteristic of the invention, at least one of the encoding algorithms is mathematically irreversible.

According to another characteristic of the invention, the method consists in creating the first and second identifiers of the individual by applying to the above-mentioned identification data an encoding algorithm and an encoding key determined in unique manner as a function of the data to be encoded.

This makes it possible to ensure that the encoded data is protected and anonymous against any attempt at decrypting, including so-called "dictionary attacks" that consist in applying a large amount of identification data to an encoding algorithm and in comparing the resulting encoded identifiers with an encoded identifier recorded in the database, for the purpose of retrieving the identity of the corresponding individual. Combining the encoding algorithm with an encoding key that varies from one individual to another, but that is always the same for a given individual, serves to ensure that a person who has knowledge of the encoding algorithm cannot gain access to the identity of an individual, unless that person also knows the encoding key that was used for creating the identifier of the individual. Since, in the method of the invention, the first identifiers which are encoded by means of an encoding algorithm and a first encoding key, are encoded again by means of an encoding algorithm and another encoding key, the anonymity of the data recorded in the database of the central unit is protected in a manner that is complete and definitive.

According to yet another characteristic of the invention, the method consists in associating with the first identifier transmitted by the local center, a number that corresponds to an order of presentation in the second identifier of the data fields of the identifier, and in creating the second identifier by encoding the fields of the first identifier in the order determined by the above-mentioned number associated with said identifier.

The second identifier comprises fields containing encoded data corresponding to the already-encoded data of the first identifier together with an additional field containing the above-mentioned number which defines the encoding order of the fields of the first identifier.

In a preferred implementation of the invention, the first identifiers of individuals as created in a local center are recorded in a database of the local center and are transmitted to the central unit after they have been selected and confirmed by an authorized person.

Preferably, data transmission between the local center and the central unit is performed using secure means.

The encoded first identifiers that are transmitted to the central unit are recorded in a database of the central unit, and are then subjected to selection and confirmation of that selection by an authorized person before being processed to create the encoded second identifiers.

In practice, provision is made for each individual whose encoded first identifier has been created in a local center to be given a card that includes said identifier and/or the identification data used for creating the identifier, which card may be of any kind, for example a smart card, or a card having a magnetic strip, a bar code, etc.

In a local center, when it is desired to access data relating to an individual for whom an identifier has been recorded in the database of that local center, then the method of the invention consists in using the encoded first identifier of the individual, as appears on the card given to the individual, or else in recreating said identifier from the identification data appearing on the card.

However, in a local center, when it is necessary to access data concerning an individual, but recorded in the database of another local center for collecting data, then the method of the invention consists in recreating the encoded first identifier of the individual and in using it to search for data relating to said individual.

When an individual accompanied by a doctor seeks to access data relating to the individual and recorded in the database of the central unit, the method of the invention consists in sending to the central unit the encoded first identifier of the individual, as recreated or as input from the card given to the individual, together with a request to generate the encoded second identifier within a given period, in verifying that no significant modification has been made to the data since the request for access, and on condition that no such modification has been made, in informing the requester that the data is available and in requesting the requester to reconnect to the central unit in order to consult the data.

This procedure thus makes it possible to comply with the French law of Mar. 4, 2002 relating to patients and the quality of the hospital system, whereby a patient must be able to access data concerning that patient, not only with the help of the patient's doctor, but also directly, after a cooling-off period of 48 hours between the request for access and the information being handed over, where such handover cannot take place sooner than 48 hours after any significant modification is made to said information.

The method of the invention is applicable not only to processing medical data relating to individuals, but also to processing administrative, tax, or other data relating to individuals, whenever it is useful or necessary to make use of a family dimension, e.g. in the fields of tax collection, insurance, asset management, etc.

BRIEF DESCRIPTION OF THE DRAWINGS

The invention can be better understood and other characteristics, details, and advantages thereof appear more clearly on reading the following description made by way of example with reference to the accompanying drawings, in which.

MORE DETAILED DESCRIPTION

Figure 1:
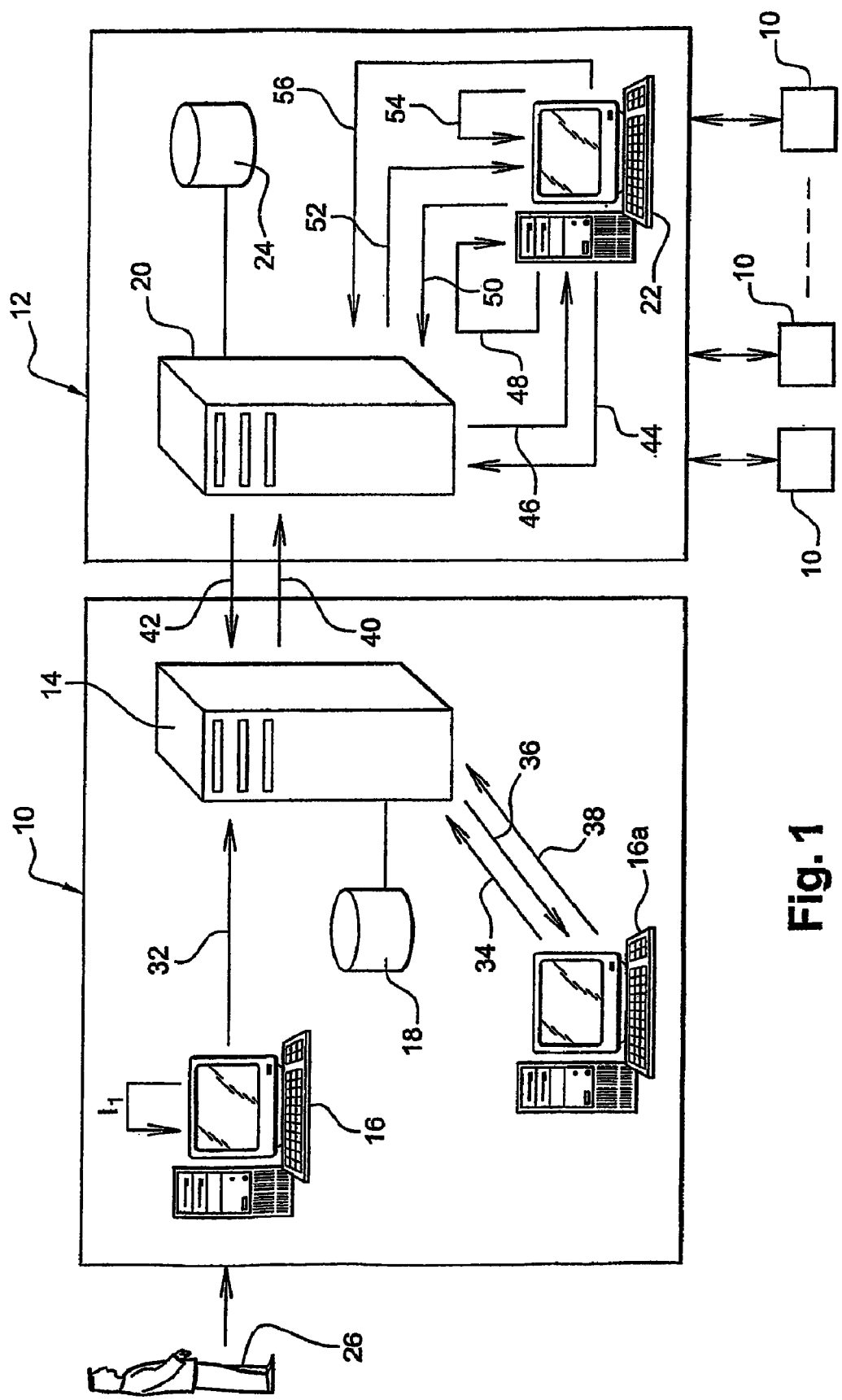
FIG. 1 is a diagram showing the main steps of creating first and second encoded identifiers in accordance with the invention.

Reference is made initially to FIG. 1, in which reference 10 designates a local center for collecting data, which is connected by information transmission means, such as a telecommunications network, for example, to a central unit 12 also connected by said data transmission means to a plurality of other local centers 10 for collecting data.

Each local center 10 comprises a server 14 having connected thereto terminals 16 and a local database 18.

The central unit 12 comprises a server 20 having connected thereto terminals 22 and a central database 24.

When a patient 26 goes to a local center 10 for collecting data, a first encoded identifier I1 of the individual is created by inputting identification data of the individual via a terminal 16 installed in the reception office of the local center 10.

The identification data of the individual 26 comprises that person's surname (as at birth and not a customary surname or a married surname), given name (i.e. the first name entered in the birth registry and not a nickname or a second or third given name), and date of birth, together with the surnames, first names, and dates of birth of that individual's father and mother.

Preferably, in order to ensure that the input is reliable, the individual 26 should hand over to the person inputting data on the terminal 16 a civil status record or any other document reliably identifying the individual 26 and his or her father and mother.

Individuals 26 not having a document of that kind available should be asked to come back with the document in question or to cause it to be delivered to the local center 10 in order to verify the data that has been input.

Furthermore, data should be input on the terminal 16 using a procedure that includes giving a quality level to the data being input, such a quality level taking account, for example, of the presentation or non-presentation of an individual's identity card, the identity, level of competence, etc., of the person inputting the data.

In the event of a risk of confusion between two individuals, this serves in particular to enable the quality level of the identification data input to be consulted in order to determine which input is the less reliable and launch a verification operation on the data input with the lower quality level, prior to confirming or not confirming a chain making use of the data.

When the identification data of an individual has been input on a terminal 26, provision can also be made for the data to be printed out so that the individual can verify that it is exact. Once data input has been confirmed, the first encoded identifier I1 corresponding to the individual 26 is created and a card including this identifier, possibly together with the corresponding identification data, is handed to the individual 26, the card being, for example, a smart card, a card with a magnetic strip, a card having data printed in the clear or in the form of a bar code, etc.

The first encoded identifier I1 is encoded as follows:

An encoding algorithm is applied, and preferably a first encoding key having three triplets of variables made up of the identification data corresponding to the individual and to his or her father and mother. By way of example, the encoding algorithm is a hashing algorithm such as the standard hash algorithm (SHA) that is mathematically irreversible. The three identification data items of an individual (surname, first name, and date of birth) are hashed individually in order to retain a high level of security and also in order to make it possible subsequently, when chaining, to identify possible input errors and missing data (e.g. in the event of the date of birth of an individual not being known).

A first encoding key is associated with this algorithm and is determined as a function of the data to be encoded so as to be unique for that data. For example, this encoding key is obtained from a matrix of characters recorded in a file known as the "key file". For each data item to be hashed, the characters that are to constitute the specific key associated with hashing that item are selected from the file by an algorithm that takes account of the length of the data item and of the values and the positions of the characters making up the data item. The key file containing the characters from which the encoding key is constituted is itself generated in random manner.

The encoding key K1 serves to scramble the encoding algorithm in order to counter "dictionary attacks" as mentioned above.

The result of the encoding corresponds to concatenating the results of encoding the different variables constituted by the identification data items of the individual and his or her father and mother.

The encoded identifier I1 is generated on the terminal 16, and then a record of the data as input and confirmed is sent to the local database 18 by the server 14, and subsequently when a dossier closure request is generated from the terminal 16, the data that has been transferred to the database 18 is deleted from the terminal 16.

Thereafter, a person in charge of the local center 10 requests, e.g. from another terminal 16a, the list of the data that has been recorded in the local database 18 and that has not been transmitted to the central unit 12. This data is transferred by the server 14 to the terminal 16a of the person in charge, who selects the data for transferring to the central unit 12 and confirms the selection.

Thereafter, the server 14 searches in the local database 18 for the data relating to each individual that is to be transferred, and creates one file per individual. The file is transferred to the central unit 12 by the usual data transmission means, e.g. by a telecommunications network, with transmission preferably taking place in secure manner.

The data relating to an individual and transferred to the central unit 12 comprises the first encoded identifier I1 of the individual, an order number which is the registration number of the data in the database 18, and an identifier of the local center 10, this identifier possibly being the identifier of the person in charge of the local center. The corresponding medical data is naturally also transferred together with the identification data.

On receiving this data, the server 20 of the central unit 12 delivers an acknowledge of receipt to the server 14 of the local center 10 and records the data it has just received in the central database 24.

A person in charge or an entitled person of the central unit 12 uses a terminal 22 to request from the server 20 the list of the data that has recently been received and that has not yet been processed, and in return receives this list on the terminal 22.

The person in charge or the entitled person then selects the data that is to be processed and confirms the selection, this confirmation leading to an integer being generated for each individual concerned, the integer lying in the range 0 to 999999 and corresponding to the order in which the data fields constituting the first encoded identifier I1 are to be encoded in the central unit.

When the identifier comprises nine data fields (three data fields identifying the individual, three data fields identifying the father, and three data fields identifying the mother), the number of possible combinations of these nine fields is equal to 9!, i.e. 362880. A correspondence table between each possible combination and a six-digit number is then used. The correspondence table is initialized in random manner, thus making it possible to make use of the entire available range of numbers (0 to 999999) without being restricted to numbers lying in the range 0 to 362880.

The list of selected individuals and the corresponding numbers are sent from the terminal 22 to the central database 24 which, for each selected individual, returns to the terminal 22 the first encoded identifier I1 of that individual and the above-mentioned number associated with the order of the nine fields to be encoded in order to generate the second identifier I2 of the individual.

This second identifier I2 is generated from a hashing algorithm that can be the same as that used in the local center 10 and from an encoding key K2 that is available solely on the terminal 22 of the above-mentioned person in charge or entitled person, said encoding key K2 being generated on the same principles as the first encoding key K1.

The second encoded identifier I2 of the individual comprises ten data fields, these first nine fields containing the encoded identification data, and the tenth field containing the integer that defines the order of the first nine fields.

Once the encoded second identifiers I2 have been generated on the terminal 22, they are sent to the server 20 of the central unit together with the corresponding encoded first identifiers I1. The server 20 then overwrites the values of the encoded first identifiers I1 with the values of the corresponding encoded second identifiers I2. Thereafter, the corresponding data is deleted from the terminal 22 of the person in charge or the entitled person. A correspondence table between the order number of the encoded first identifier I1 (or the registration number of the data in the local database 18), the identification of the local center 10, and the encoded second identifier I2 is created in order to facilitate establishing a possible connection with the local center 10 in the event of a chaining problem.

When the encoded second identifier I2 has been recorded in the central database 24, it becomes possible to establish individual family chains relating to that identifier by comparison with the encoded second identifiers already recorded in the database 24.

These chains are made up by the server 20 and serve to construct the family tree of an individual, from a vertical point of view, i.e. connecting that individual to ancestors and descendants, and from a horizontal point of view, i.e. connecting that individual to any brothers and sisters by sorting the dates of birth of individuals having the same parents, to any half-brothers and half-sisters by sorting the dates of birth of individuals having a father or a mother in common, and also to determine childless couples (by reading the fields corresponding to the spouse in the family identifier, stillbirths and sterility being obtained from the medical data contained in the dossiers of the individuals).

Individual chaining consists in grouping together data coming from a plurality of different local centers and relating to the same individual. When the same identifier is found associated with different sets of data, the data can be merged, since in principle it relates to the same individual, but only after verification in order to detect possible inputting errors and to correct them.

For individual chains, all nine data fields constituting an encoded identifier might not necessarily be used, the selection of which fields are used depending on data missing from certain fields and also on the quality of the data as initially recorded.

In accordance with the laws in force in France, an individual has a right of access to his or her own medical information, under certain conditions.

Figure 2:
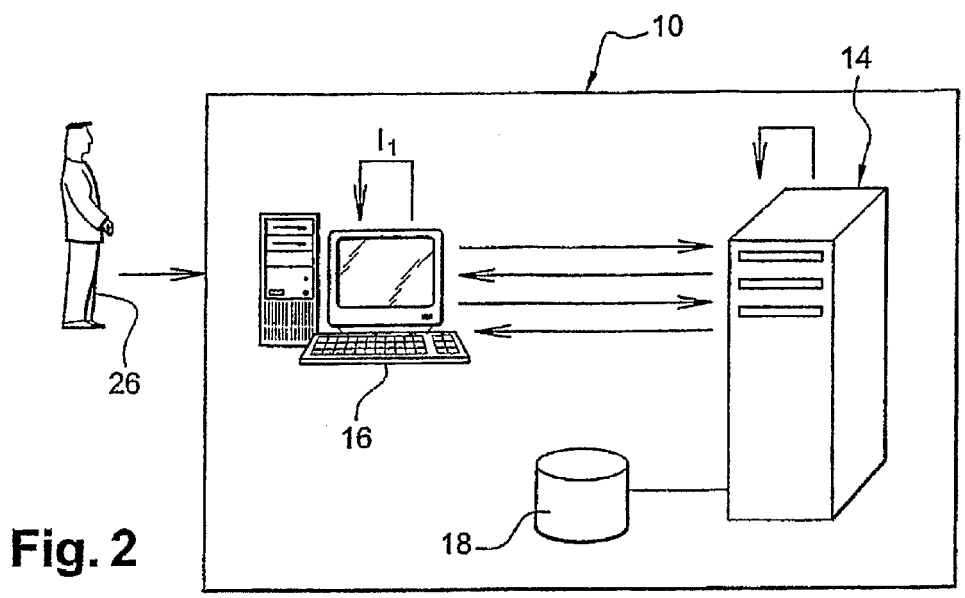
FIG. 2 is a diagram showing the main steps of accessing a file recorded in a local database.

When individuals 26 go to a local center 10 where they have previously been registered, they can in principle present a card to reception (FIG. 2). If an encoded first identifier I1 appears on the card, that identifier is input via the terminal 16 at reception and is transmitted to the local server 14 which searches for the corresponding dossier in the local database 18. When the server 14 finds the dossier, it transmits the corresponding administrative dossier to the terminal 16 at reception. If the server 14 does not find the corresponding dossier, then there has been an error in inputting the identifier, assuming it was input manually.

If the card held by an individual does not have that individual's encoded identifier, but only the identification data of that individual and his or her parents, then that data is input manually or by reading a bar code, and the first encoded identifier I1 is generated anew by the terminal 16 and sent to the server 14 which searches for the corresponding dossier in the database 18.

When an individual who has already been registered in a local center 10 goes to another local center 10 to access his or her own medical data, then reception in that other center proceeds by creating a dossier and an encoded identifier as described with reference to FIG. 1, which identifier ought to correspond to the identifier that has already been created in the first center. The looked-for data is obtained via the central unit 2.

A doctor can use the terminal 16 at the reception desk of a local center 10 to access patient data recorded in the local database 18 of the local center. Using the terminal 16, the doctor sends the identification data of the patient to the server 14 and the server 14 searches for a corresponding dossier in the local database 18 and informs the doctor of the results of the search on the terminal 16, after which the doctor returns via the terminal 16 to the server 14 a request to consult the dossier, which is then transmitted to the doctor by the server 14.

Figure 3:
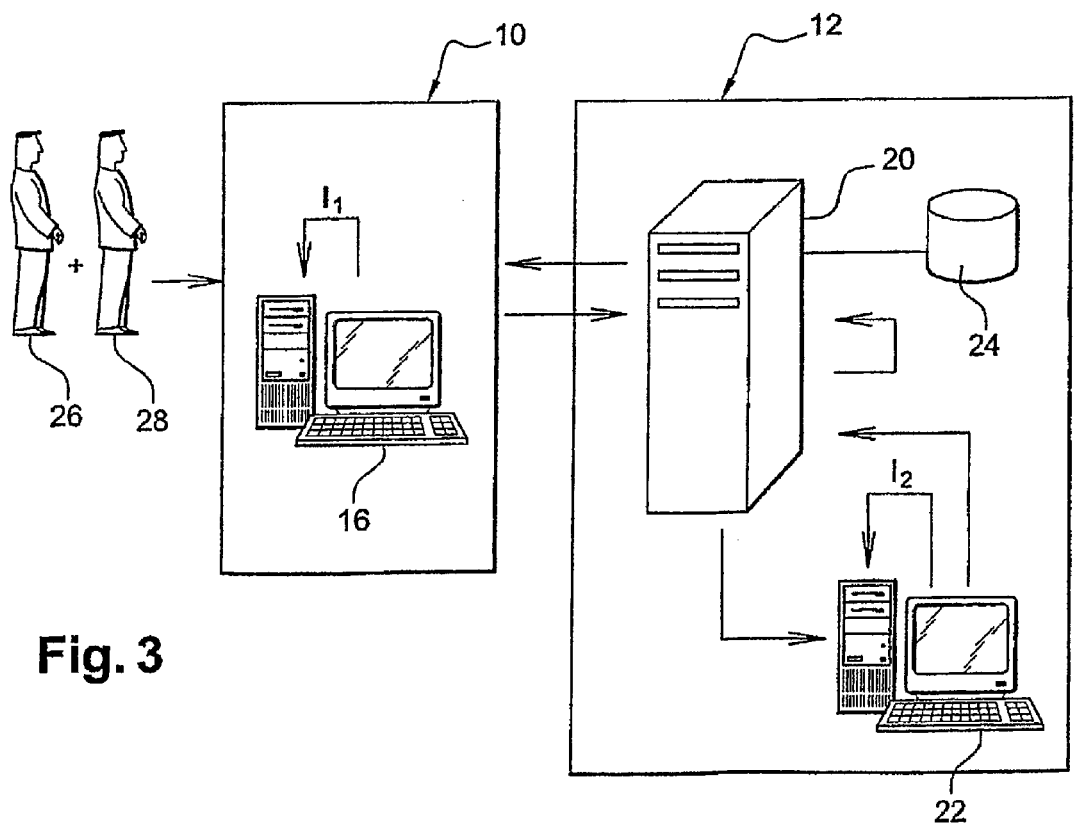
FIG. 3 is a diagram showing the main steps of accessing data recorded in a central database.

An individual 26 may also have access to his or her own medical data, that has been recorded in the database 24 of the central unit 12. To do this, as shown in FIG. 3, the individual may be accompanied by a doctor 28 who might already have a family dossier concerning the individual 26, recorded in the database 24 of the central unit 12 and to which the doctor can have access in conventional manner.

If the doctor does not have such a dossier for the patient, the doctor needs to use a terminal 16 of a local center 10 to generate in the above-described manner the encoded first identifier I1 of the individual 26 and transmit it to the server 20 of the central unit 12, sending to the person in charge or the entitled person of said central unit a request to generate the encoded second identifier I2 of the individual 26 within a period that is, for example, a maximum of five working days and a minimum of 48 hours, providing no significant modification to the medical data concerning the individual 26 is recorded after the request for access and no prohibition on the data being consulted by the individual has previously been made by a doctor.

The request to consult the data is transmitted by the server 20 to the terminal 22 of the person in charge or the entitled person and generates on that terminal the encoded identifier I2 of the individual 26 which is sent to the server 20. The server verifies that no significant modification of the medical data has taken place and that the dossier has not been subjected to a prohibition on consultation by the patient, after which the server sends to the terminal 16 of the local center 10 information that the dossier is available and invites the doctor 28 to reconnect to the server 20 in a given period.

The doctor 28 can then use the terminal 16 of the local center 10 to reconnect to the server 20 and access the patient's dossier contained in the database 24.

When a doctor connects to the server 20 of the central unit 12 without being accompanied by a patient, the doctor has write access only to data concerning the patient that the doctor has him- or herself transmitted to the central unit 12. The doctor can access the other data relating to the patient and contained in the database 24, but in read-only mode.

If the doctor desires to access any other data relating to the patient as transferred by other local centers 10, then it is necessary to make a request to consult the individual chain of data relating to the patient starting from the patient's dossier.

Figure 4:
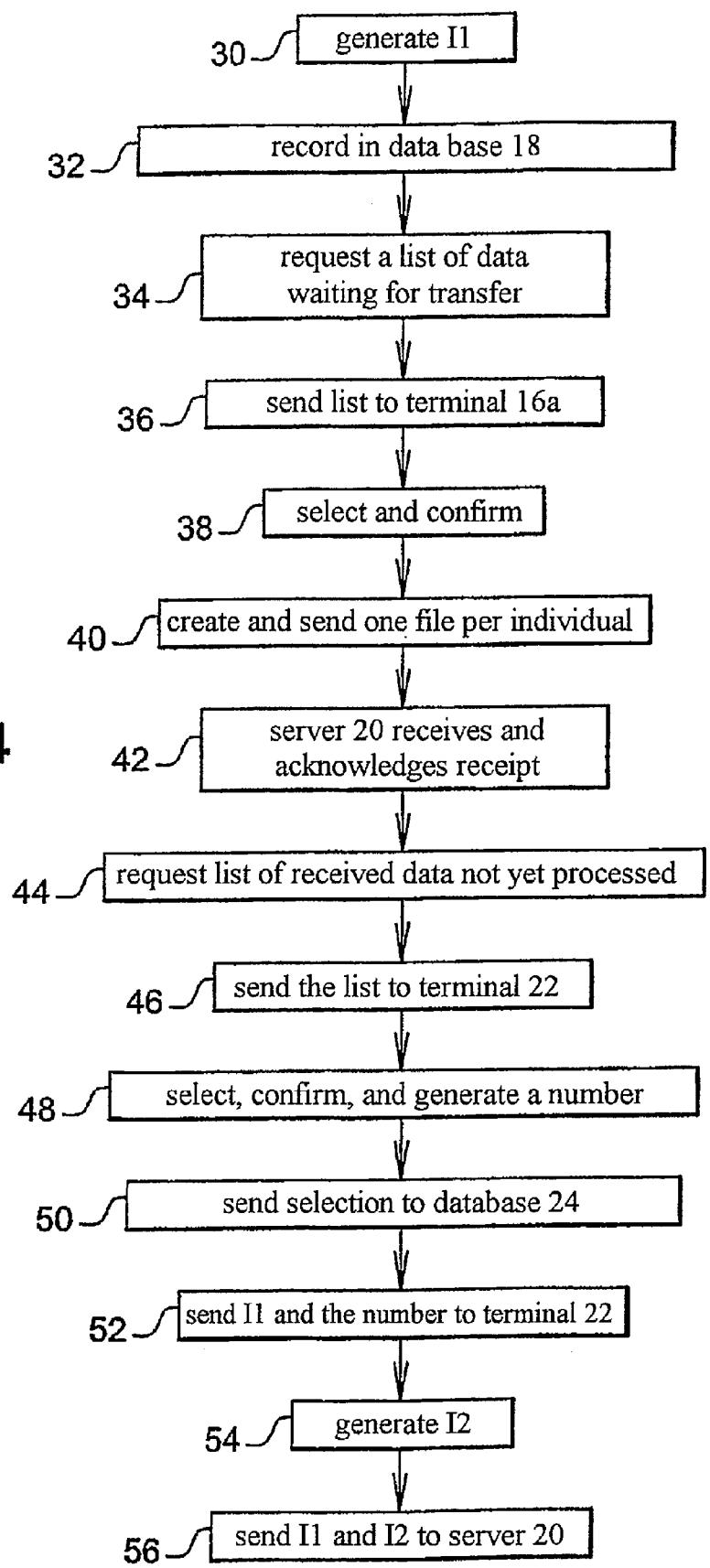
FIG. 4 is a flow chart showing diagrammatically the main steps of the method of the invention.

The main steps in generating the encoded first and second identifiers of an individual are summarized in the flow chart of FIG. 4.

The first step 30 consists in generating the encoded first identifier I1 on the terminal 16 at the local center 10 on the basis of the surname, the first name, and the date of birth of the individual 26, the surnames, first names, and dates of birth of the individual's father and mother, and of the encoding key K1 associated with said data.

The second step 32 consists in recording the data as input and confirmed in the local database 18 together with the encoded first identifier I1 of the individual.

The third step 34 is a request made by the person in charge of the local center 10 for a list of data waiting to be transferred to the central unit 12.

The following step 36 consists in the server 14 sending said list to the terminal 16a of the person in charge.

The following step 38 consists in the person in charge selecting data for transfer and in confirming the selection.

The following step 40 consists in the local server 14 creating one file per individual, each file comprising the encoded first identifier I1, an order number, and the identification of the local center 10 or the person in charge, and sending said file to the central unit 12 over a secure connection.

The following step 42 consists in the server 20 of the central unit 12 receiving the file and acknowledging its receipt to the local server 14.

The following step 44 is a request made by the person in charge on the terminal 22 for the list of data that has been received but not yet processed.

In the following step 46, the list is sent by the server 20 to the terminal 22 of the person in charge.

In the following step 48, the person in charge selects the data to be processed, thereby causing an integer to be generated for each individual involved, the number lying in the range 0 to 999999 and corresponding to the encoding order of the nine fields of the encoded first identifier I1.

The following step 50 is sending a list of selected individuals together with the respective associated numbers from the terminal 22 to the database 24 via the server 20.

In the following step 52, the server 20 sends to the terminal 22 the encoded first identifier I1 of each selected individual together with the associated number representing the encoding order of the fields of said identifier in the second identifier I2.

The following step 54 is the terminal 22 generating the encoded second identifier I2 from the second encoding key K2 and the data fields constituting the encoded first identifier I1.

The following step 56 is sending the encoded second identifier I2 and the first identifier I1 to the server 20 which then replaces the values of I1 by the values of I2 and deletes the corresponding data from the terminal 22 of the person in charge and draws up a correspondence table between the arrival order of I1, the local center 10 that sent I1, and the encoded second identifier I2.

After I2 and the values of the correspondence table have been recorded in the database 24, the server 20 of the central unit 12 can proceed automatically in establishing family and individual chains of the data from the identifier I2 newly recorded in the database 24.

For greater clarity, the references of the main steps 30 to 56 of the method of the invention are marked in FIG. 1.

What is claimed is:

1. A method of identifying data relating to individuals in order to establish chains of said data by means of servers, databases, and data transmission means, the method consisting in:

using a data processor system comprising local centers for collecting data, each having a server and a local database, a central unit for aggregating data and equipped with a server and a central database, and data transmission means between the local centers and the central unit, each local center having means for creating an encoded first identifier of an individual by applying a first encoding algorithm to identification data of the individual, the first encoded identifier including identification data comprising the individual's surname, first name, and date of birth, and identification data of the individual's father and mother, comprising their surnames, first names, and dates of birth;

in using the above-mentioned transmission means to transmit said encoded first identifier with a registration number and an identifier of the local center to the central unit which includes means for creating an encoded second identifier of the individual by applying a second encoding algorithm to the encoded first identifier, and to record the encoded second identifier in the central database in the place of the encoded first identifier, together with the correspondence between the second identifier, said registration number of the first identifier, and the identifier of the local center, wherein the second identifier of the individual includes encoded identification data comprising the individual's surname, first name, and date of birth, and encoded identification data of the individual's father and mother, comprising their surnames, first names, and dates of birth;

comparing the second identifier of the individual with second identifiers of other individuals in the central unit to determine if the identification data of the individual and/or of the individual's father and mother are shared with identification data of others;

chaining the identification data of the individual to identification data of one or more others if the same identification data of the individual and/or of the individual's father and/or mother are shared with said one or more others.

2. A method according to claim 1, wherein said first or second encoding algorithm is mathematically irreversible or both first and second encoding algorithms are mathematically irreversible.

3. A method according to claim 1, consisting in creating each of said first and second identifiers of the individual by applying said first or second encoding algorithm and an encoding key determined in unique manner as a function of the data to be encoded.

4. A method according to claim 3, consisting in using identical first and second encoding algorithms and different encoding keys for creating the above-mentioned first and second identifiers.

5. A method according to claim 1, consisting in associating with the first identifier transmitted by the local center, a number that corresponds to an order of presentation in the second identifier of the data fields of the first identifier, and in creating the second identifier by encoding the fields of the first identifier in the order determined by the above-mentioned number associated with said identifier.

6. A method according to claim 5, wherein the second identifier comprises fields containing encoded data corresponding to the already-encoded data of the first identifier together with an additional field containing the above-mentioned number which corresponds to an order of presentation in the second identifier of the data fields of the first identifier.

7. A method according to claim 1, wherein the first identifiers created in the local center are recorded in the database of the local center and are transmitted to the central unit after being selected and confirmed by an authorized person.

8. A method according to claim 1, wherein the first identifiers transmitted to the central unit are recorded in the central database and are then subjected to selection and selection confirmation by an authorized person prior to being processed in order to create second identifiers.

9. A method according to claim 1, wherein data transmission between the local center and the central unit makes use of secure means.

10. A method according to claim 1, consisting in giving the individual for whom a first identifier has been created, a card that includes said identifier and/or the identification data used for creating the identifier.

11. A method according to claim 1, wherein, in order to access in a local center data concerning an individual whose identifier has been recorded in the database of said local center, the method consists in using the first identifier of the individual that appears on a card given to said individual on creation of the identifier, or in recreating the identifier on the basis of the identification data of said individual and that of the individual's father and/or mother by applying said first encoding algorithm, or in using the identification data of the individual.

12. A method according to claim 1, wherein, in order to access in a local center data concerning an individual for whom an identifier has been recorded in a local database of another local center, the method consists in recreating the first identifier of the individual and in using it to search via the central unit for data concerning said individual and recorded in said other local center.

13. A method according to claim 1, wherein, in order to access data concerning an individual that has been recorded in the database of the central unit, the method consists in sending to the central unit the first identifier of the individual as recreated or as appears on the card given to the individual, together with a request to generate the second identifier within a given period, in verifying that no modification to the data has taken place since the request for access to the data, and if no such modification has taken place, in informing the requester that the data is available and in asking the requester to reconnect to the central unit to consult the data.

14. A method according to claim 1, consisting in associating a quality level with the identification data input in a local center in order to create an encoded first identifier of an individual, in comparing the quality level of information that has been input with a threshold to be determined, and in verifying the input data when the quality level is lower than said threshold.

15. A method of identifying data relating to individuals in order to establish chains of said data by means of servers, databases, and data transmission means, the method consisting in:

using a data processor system comprising local centers for collecting data, each having a server and a local database, a central unit for aggregating data and equipped with a server and a central database, and data transmission means between the local centers and the central unit, each local center having means for creating an encoded first identifier of an individual by applying a first encoding algorithm to identification data of the individual, comprising the individual's surname, first name, and date of birth, and to identification data of the individual's father and mother, comprising their surnames, first names, and dates of birth;

in using the above-mentioned transmission means to transmit said encoded first identifier with a registration number and an identifier of the local center to the central unit which includes means for creating an encoded second identifier of the individual by applying an encoding algorithm to the encoded first identifier, and to record the encoded second identifier in the central database in the place of the encoded first identifier, together with the correspondence between the second identifier, said registration number of the first identifier, and the identifier of the local center; and comparing the second identifiers in the central unit in order to determine if the identification data of the individual and/or of the individual's father and mother are shared with identification data of others, and chaining the identification data of the individual to identification data of one or more others if the same identification data of the individual and/or of the individual's father and/or mother are shared with said one or more others, wherein the first identifiers transmitted to the central unit are recorded in the central database and are then subjected to selection and selection confirmation by an authorized person prior to being processed in order to create second identifiers.

\* \* \* \* \*

UNITED STATES PATENT AND TRADEMARK OFFICE
CERTIFICATE OF CORRECTION

PATENT NO. : 8,229,764 B2
APPLICATION NO. : 11/683003
DATED : July 24, 2012
INVENTOR(S) : Cohen et al.

It is certified that error appears in the above-identified patent and that said Letters Patent is hereby corrected as shown below:

Title page,
Item "(73) Assignee: Universite de Bourgogne, Dijon Cedex (FR)" should read
Item --(73) Assignee: Olivier Cohen, Grenoble (FR)--.

Signed and Sealed this
Fifth Day of February, 2013

Teresa Stanek Rea
*Acting Director of the United States Patent and Trademark Office*